United States Patent
Li et al.

(10) Patent No.: US 11,719,660 B1
(45) Date of Patent: Aug. 8, 2023

(54) SOLID STATE CARBON DIOXIDE SENSOR

(71) Applicant: United States of America as Represented by the Administrator of NASA, Washington, DC (US)

(72) Inventors: Jing Li, San Jose, CA (US); Ami Milan Hannon, Scotts Valley, CA (US)

(73) Assignee: United States of America as Represented by the Administrator of NASA, Washington, DC (US)

( * ) Notice: Subject to any disclaimer, the term of this patent is extended or adjusted under 35 U.S.C. 154(b) by 287 days.

(21) Appl. No.: 16/924,998

(22) Filed: Jul. 9, 2020

Related U.S. Application Data

(60) Provisional application No. 62/936,379, filed on Nov. 15, 2019.

(51) Int. Cl.
*G01N 27/12* (2006.01)
*G01N 33/00* (2006.01)

(52) U.S. Cl.
CPC ......... *G01N 27/127* (2013.01); *G01N 33/004* (2013.01)

(58) Field of Classification Search
CPC ........................... G01N 27/127; G01N 33/004
See application file for complete search history.

(56) References Cited

U.S. PATENT DOCUMENTS

| | | | |
|---|---|---|---|
| 2016/0047773 A1* | 2/2016 | Selvaganapathy | G01N 33/182 204/422 |
| 2020/0088668 A1* | 3/2020 | Swager | C08F 226/06 |
| 2022/0163473 A1* | 5/2022 | Bartsch | G01N 33/0039 |

OTHER PUBLICATIONS

Hannon, A., & Li, J. (2019). Solid state electronic sensors for detection of carbon dioxide. Sensors, 19(18), n/a. (Year: 2019).*

\* cited by examiner

*Primary Examiner* — Alvaro E Fortich
*Assistant Examiner* — Adam S Clarke
(74) *Attorney, Agent, or Firm* — Rhys W. Cheung; Robert M. Padilla

(57) ABSTRACT

A solid state, carbon dioxide ($CO_2$) sensor configured for sensitive detection of $CO_2$ in both dry and moist conditions. The $CO_2$ sensor utilizes a composite sensing material that detects $CO_2$ in the range of 100 ppm to 10,000 ppm. The sensing material is composed of O-MWCNTs and a metal oxide functionalizing agent, such as iron oxide ($Fe_2O_3$) nanoparticles. The material has an inherent resistance and conductivity that is chemically modulated as the level of $CO_2$ increases. The $CO_2$ gas molecules that are absorbed into the carbon nanotube composites cause charge-transfer and changes in the conductive pathway causes changes in conductivity of the composite sensing material. This change in conductivity provides a specificity and sensitivity for $CO_2$ detection. The $CO_2$ sensor can be easily integrated into existing electronic circuitry and hardware configurations, including the hardware of a mobile computing device, such as a smart phone or tablet device.

5 Claims, 10 Drawing Sheets

SOLID STATE CARBON DIOXIDE SENSOR

CROSS-REFERENCE TO RELATED APPLICATIONS

This application claims the benefit of U.S. Provisional Application No. 62/936,379, filed Nov. 15, 2019, the contents of which are incorporated by reference as if fully set forth herewith.

ORIGIN OF INVENTION

The invention described herein was made in the performance of work under a NASA contract and by an employee of the United States Government and is subject to the provisions of Public Law 96-517 (35 U.S.C. § 202) and may be manufactured and used by or for the Government for governmental purposes without the payment of any royalties thereon or therefore. In accordance with 35 U.S.C. § 202, the contractor has elected not to retain title.

TECHNICAL FIELD

The present invention generally relates to carbon dioxide sensors.

BACKGROUND OF THE INVENTION

Monitoring carbon dioxide ($CO_2$) levels is critical because carbon dioxide displaces oxygen. The displacement of oxygen by carbon dioxide causes negative health effects. There is a great demand for effective carbon dioxide monitoring devices for a variety of applications such as monitoring global warming, measuring air quality, healthcare, mining and the food industry. In space applications, $CO_2$ detectors are very crucial at the International Space Station (ISS) for monitoring $CO_2$ levels in the crews' cabins and during $CO_2$ sequestration processes to ensure that $CO_2$ is scrubbed. It is also necessary to monitor $CO_2$ in a space suit, particularly within the astronauts' helmets.

Carbon dioxide is harmful at higher concentrations due to its ability to displace oxygen in high concentrations. There is about 0.04% (400 ppm) $CO_2$ present in normal air. Such a concentration is basically harmless. However, once the $CO_2$ concentration of inhaled air exceeds 1.0%, the $CO_2$ begins to cause harmful effects on the human body. Headaches typically start within a few hours of $CO_2$ levels of 2.0%-3.0%. At $CO_2$ levels between 4.0%-5.0%, a person begins to experience increased blood pressure and breathing issues. At $CO_2$ levels above 5.0%, a person can become incapacitated. Coma and possibly death can occur within minutes of $CO_2$ levels reaching 17%. The Occupational Safety and Health Administration (OSHA) set forth a maximum permissible exposure limit for $CO_2$ at 0.5% (5000 ppm) air composition in an eight-hour work day.

$CO_2$ toxicity is extremely dangerous for workers in confined environments. Conventional nondispersive infrared (NDIR) sensors have been used for $CO_2$ detection. An NDIR sensor works by comparing the amount of infrared light absorbed by the $CO_2$ with the amount of $CO_2$ emitted to correlate its ratio to $CO_2$ concentration. The accuracy becomes problematic when the gas absorption lines begin to broaden due to local effects of humidity. Specifically, at higher pressures, temperatures and humidity levels, radiating and collision time increase thereby causing the absorption lines to be broaden. Other conventional $CO_2$ sensors include silicon nanowires, $Sn_2O_3$, microspheres, and polymer nanofilms. However, these conventional sensors have exhibited shortcomings in range, response time, accuracy at different temperatures and pressures, power consumption and size. Furthermore, many of these conventional sensors have difficulty operating at room temperature and also have poor responses in static diffusion mode conditions.

Accurate, quick-response and low power $CO_2$ sensors are needed for many applications, such as measuring indoor air quality, modified atmospheres, stowaway detection, cellar and gas stores, marine vessels, greenhouses, monitoring landfill gas, confined spaces, cryogenics, ventilation management, mining and rebreathers (SCUBA). Accurate, quick-response and low power $CO_2$ sensors are also needed in space applications, such as space medicine, in-situ resource utilization of $CO_2$ on Mars, $CO_2$ removal in life support systems on space vessels, and monitoring the air quality in the crew's cabin. In view of the toxicity caused by inhalation of high levels of $CO_2$, what is needed is a lightweight, low cost, solid state $CO_2$ sensor that quickly provides accurate readings at different temperatures and pressures, provides for in-situ monitoring, operates at room temperature, consumes extremely low power (in the order of microwatts) and has a relatively small size.

SUMMARY OF THE INVENTION

Described herein are various exemplary embodiments of a solid state, carbon dioxide ($CO_2$) sensor configured for sensitive detection of $CO_2$ having a concentration within the range of about 100 ppm and 10,000 ppm in both dry conditions (e.g., ambient air) and high humidity conditions (e.g., >80% relative humidity). The solid state, carbon dioxide ($CO_2$) sensor achieves detection of high concentrations of $CO_2$ without saturation and in both dynamic flow mode and static diffusion mode conditions. The composite sensing material comprises oxidized multi-walled carbon nanotubes (O-MWCNT) and a metal oxide. In an exemplary embodiment, the composite sensing material comprises O-MWCNT and iron oxide ($Fe_2O_3$) nanoparticles. The composite sensing material has an inherent resistance and corresponding conductivity that is chemically modulated as the level of $CO_2$ increases. The $CO_2$ gas molecules absorbed into the carbon nanotube composites cause charge-transfer and changes in the conductive pathway such that the conductivity of the composite sensing material is changed. This change in conductivity provides a specificity and sensitivity for the $CO_2$ detection. The solid state $CO_2$ sensor of the present invention provides many benefits and advantages such a relatively light weight, small footprint and low power consumption. The solid state $CO_2$ sensor of the present invention can be easily integrated into existing electronic circuitry and hardware configurations. The solid state $CO_2$ sensor is well suited for automated manufacturing using robotics and software controlled operations. The solid state $CO_2$ sensor does not utilize consumable components or materials and does not require calibration as often as conventional $CO_2$ sensors. Since the solid state $CO_2$ sensor of the present invention can be easily integrated into existing programmable electronic systems or hardware systems, the calibration of the $CO_2$ sensor can be automated.

In some embodiments, the present invention is directed to a solid state sensor for sensing carbon dioxide ($CO_2$) comprising a substrate, electrodes disposed on the substrate and spaced apart by a predetermined distance, and a sensing material disposed over the electrodes. The sensing material comprises an oxidized carbon nanostructure having a functionalizing agent comprising iron oxide ($Fe_2O_3$). In an exemplary embodiment, the oxidized carbon nanostructure comprises O-MWCNTs. In some embodiments, the weight percentage of iron oxide ($Fe_2O_3$) in the sensing material is between about 3.25% and 3.75%. In an exemplary embodiment, the weight percentage of iron oxide ($Fe_2O_3$) in the sensing material layer is about 3.5%. The solid state ($CO_2$) sensor further comprises a plurality of electrically conductive output terminals. Each output terminal is electrically coupled to a corresponding electrode.

In some embodiments, the present invention is directed to a solid state sensor for sensing carbon dioxide ($CO_2$) comprising a substrate, a pair of interdigitated electrodes disposed on the substrate and spaced apart by a predetermined distance and sensing material disposed over the interdigitated electrodes. The sensing material comprises O-MWCNTs having a functionalizing agent comprising iron oxide ($Fe_2O_3$). In some embodiments, the weight percentage of iron oxide ($Fe_2O_3$) in the sensing material is between about 3.25% and 3.75%. In an exemplary embodiment, the weight percentage of iron oxide ($Fe_2O_3$) in the sensing material is about 3.5%. The solid state ($CO_2$) sensor further comprises a pair of electrically conductive output terminals. Each output terminal is electrically coupled to a corresponding interdigitated electrode. The solid state ($CO_2$) sensor further comprises a circuit electrically connected between the pair of electrically conductive output terminals to provide electrical power to the pair of interdigitated electrodes and to detect and measure the current flow through the pair of interdigitated electrodes.

In some embodiments, the present invention is directed to a method of fabricating a solid state sensor for sensing carbon dioxide, comprising providing a substrate, disposing a pair of electrodes on the substrate, providing a predetermined amount of multi-walled carbon nanotubes (MWCNTs), and oxidizing the MWCNTs with a mixture of acids at a first predetermined temperature and a first predetermined amount of time to produce O-MWCNTs. The method further comprises diluting, decanting and centrifuging the O-MWCNTs, rinsing the O-MWCNTs in water to produce purified O-MWCNTs and drying the purified O-MWCNTs at a second predetermined temperature for a second predetermined amount of time to produce purified O-MWCNTs in dry powder form. The method further comprises forming a solution consisting of water, the purified O-MWCNTs and iron oxide ($Fe_2O_3$) nanoparticles so as to produce a uniform suspension, depositing the uniform suspension onto the electrodes, and thereafter, baking the substrate so as to transform the uniform suspension into a dry ($CO_2$) sensing material.

In some embodiments, the present invention is directed to an internal carbon dioxide ($CO_2$) sensor that comprises a substrate, electrodes disposed on the substrate and spaced apart by a predetermined distance and a sensing material disposed over the electrodes such that the sensor is electrically, electronically, or communicatively coupled to a mobile computing device, such as a smart phone, tablet, or other mobile computing device running a mobile operating system, such as Apple, Inc.'s iOS or Google, Inc.'s Android operating system. The sensing material comprises an oxidized carbon nanostructure having a functionalizing agent comprising iron oxide ($Fe_2O_3$). In an exemplary embodiment, the oxidized carbon nanostructure comprises O-MWCNTs. The internal carbon dioxide sensor further comprises a plurality of electrically conductive output terminals. Each output terminal is electrically coupled to a corresponding electrode.

Programmable internal electronic circuitry in the mobile computing device includes data acquisition circuitry that is coupled to the electrically conductive output terminals of the carbon dioxide sensor and configured for detecting and measuring the electrical current flow through the electrodes. The mobile computing device is programmed with an application program (i.e., mobile app) that when executed, is configured to determine if the detected current flow represents a concentration of carbon dioxide that exceeds a predetermined concentration of carbon dioxide, and alerts a user if it is determined that the concentration of carbon dioxide exceeds the predetermined concentration of carbon dioxide. The programmable internal electronic circuitry also may also run the operating system of the mobile computing device, including executing and implementing other smart phone functionality. In other words, the sensor may be integrated into or with the internal electronic circuitry or other hardware components of a smart phone or other mobile computing device. In some embodiments, the weight percentage of iron oxide ($Fe_2O_3$) in the sensing material is between about 3.25% and 3.75%. In an exemplary embodiment, the weight percentage of iron oxide ($Fe_2O_3$) in the sensing material layer is about 3.5%.

Certain features and advantages of the present invention have been generally described in this summary section. However, additional features, advantages and embodiments are presented herein or will be apparent to one of ordinary skill of the art in view of the drawings, specification and claims hereof. Accordingly, it should be understood that the scope of the invention shall not be limited by the particular embodiments disclosed in this summary section.

DETAILED DESCRIPTION OF THE INVENTION

Figure 1A:
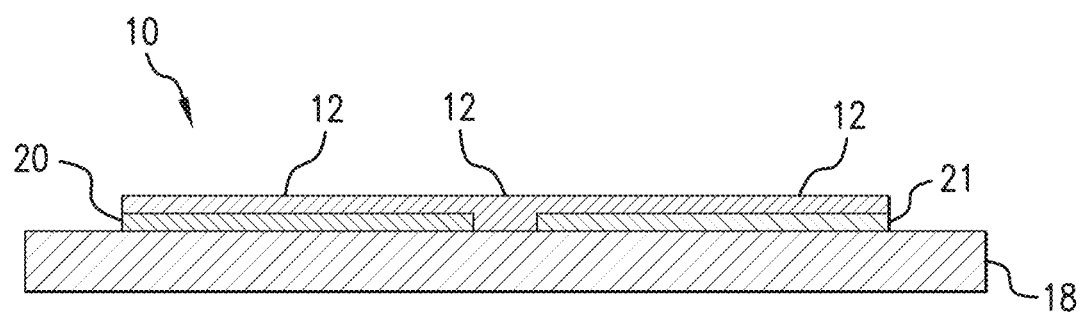
FIG. 1A is a cross-sectional view of a solid state carbon dioxide sensor in accordance with some embodiments of the present invention.

The present invention may be understood more readily by reference to the following detailed description taken in connection with the accompanying figures and examples, which form part of this disclosure. It is to be understood that this invention is not limited to the specific devices, methods, conditions or parameters described and/or shown herein, and that the terminology used herein is for the purpose of describing particular embodiments by way of example only and is not intended to be limiting of the claimed invention. As used herein, the terms "comprises," "comprising," "includes," "including," "has," "having" or any other variation thereof, are intended to cover a non-exclusive inclusion. For example, a process, method, article or apparatus that comprises a list of elements is not necessarily limited to only those elements, but may include other elements not expressly listed or inherent to such process, method, article or apparatus. Also, as used in the specification including the appended claims, the singular forms "a," "an," and "the" include the plural. Any numerical parameters set forth in the specification and attached claims are approximations (for example, by using the term "about") that may vary depending upon the desired properties sought to be obtained by the present invention. All ranges of numerical values are inclusive.

It is to be appreciated that certain features of the invention which are, for clarity, described herein in the context of separate embodiments, may also be provided in combination in a single embodiment. Conversely, various features of the invention that are, for brevity, described in the context of a single embodiment, may also be provided separately or in any sub-combination.

As used herein, the abbreviation "MWCNT" shall refer to "multi-walled carbon nanotube" and the abbreviation "MWCNTs" shall refer to "multi-walled carbon nanotubes".

As used herein, the abbreviation "O-MWCNT" shall refer to "oxidized multi-walled carbon nanotube" and the abbreviation "O-MWCNTs" shall refer to "oxidized multi-walled carbon nanotubes".

In accordance with one embodiment of the present invention, the components, process steps, and/or data structures may be implemented using various types of operating systems (OS), computing platforms, firmware, computer programs, computer languages, and/or general-purpose machines. The method can be run as a programmed process running on processing circuitry. The processing circuitry can take the form of numerous combinations of processors and operating systems, or a stand-alone device. The process can be implemented as instructions executed by such hardware, hardware alone, or any combination thereof. The software may be stored on a program storage device readable by a machine.

In addition, those of ordinary skill in the art will recognize that devices of a less general purpose nature, such as hardwired devices, field programmable logic devices (FPLDs), including field programmable gate arrays (FPGAs) and complex programmable logic devices (CPLDs), application specific integrated circuits (ASICs), or the like, may also be used without departing from the scope and spirit of the inventive concepts disclosed herein.

In accordance with one embodiment of the present invention, the method may be implemented on a data processing computer such as mobile computing device, a personal computer, workstation computer, mainframe computer, or high performance server running an OS such as Solaris® available from Oracle Corporation of Redwood City, Calif., Microsoft® Windows®, available from Microsoft Corporation of Redmond, Wash., various versions of the Unix operating system such as Linux available from a number of vendors, various embedded operating systems, or various mobile operating systems. The method may also be implemented on a multiple-processor system, or in a computing environment including various peripherals such as input devices, output devices, displays, pointing devices, memories, storage devices, media interfaces for transferring data to and from the processor(s), and the like.

The features, structures, or characteristics of the invention described throughout this specification may be combined in any suitable manner in one or more embodiments. For example, reference throughout this specification to "certain embodiments," "some embodiments," or similar language means that a particular feature, structure, or characteristic described in connection with the embodiment is included in at least one embodiment of the present invention. Thus, appearances of the phrases "in certain embodiments," "in some embodiment," "in other embodiments," or similar language throughout this specification do not necessarily all refer to the same group of embodiments and the described features, structures, or characteristics may be combined in any suitable manner in one or more embodiments.

It should be noted that reference throughout this specification to features, advantages, or similar language does not imply that all of the features and advantages that may be realized with the present invention should be or are in any single embodiment of the invention. Rather, language referring to the features and advantages is understood to mean that a specific feature, advantage, or characteristic described in connection with an embodiment is included in at least one embodiment of the present invention. Thus, discussion of the features and advantages, and similar language, throughout this specification may, but do not necessarily, refer to the same embodiment.

Furthermore, the described features, advantages, and characteristics of the invention may be combined in any suitable manner in one or more embodiments. One skilled in the relevant art will recognize that the invention can be practiced without one or more of the specific features or advantages of a particular embodiment. In other instances, additional features and advantages may be recognized in certain embodiments that may not be present in all embodiments of the invention.

In certain aspects of the present invention, there are provided composite solid state $CO_2$ sensors that are composed of O-MWCNTs and iron-oxide ($Fe_2O_3$) nanoparticles. The composite solid state $CO_2$ sensor of the present invention has high $CO_2$ sensitivity and can measure in the range of about 100 ppm-10000 ppm $CO_2$. The maximum permissible $CO_2$ exposure limit is 5,000 ppm which has been set by OSHA. The composite solid state $CO_2$ sensor of the present invention exhibits up to about five (5) times higher sensitivity to carbon dioxide than conventional MWCNT-based sensors that do not utilize any iron-oxide particles. The composite solid state $CO_2$ sensor of the present embodiments has a rapid response time and provides sensor outputs in seconds. The composite solid state $CO_2$ sensor of the present embodiments also exhibits rapid recovery, decreased noise and reproducibility of responses.

Carbon nanotubes (CNTs) have a structure allowing the entire surface of the carbon nanotube to be available for gas adsorption. As a result, the carbon nanotube exhibits high sensitivity, down to <1 ppb, and can react to a single foreign molecule. The electrical characteristics of carbon nanotubes are heavily influenced by gases that donate or accept electrons. $CO_2$ is a weak oxidizing gas. Thus, once $CO_2$ interacts with the carbon nanotubes, the $CO_2$ will take electrons from the carbon nanotubes. The loss of electrons from the carbon nanotubes is reflected in a measurable resistance change of the carbon nanotubes. Carbon nanotubes have a very high surface area to volume ratio.

Figure 1B:
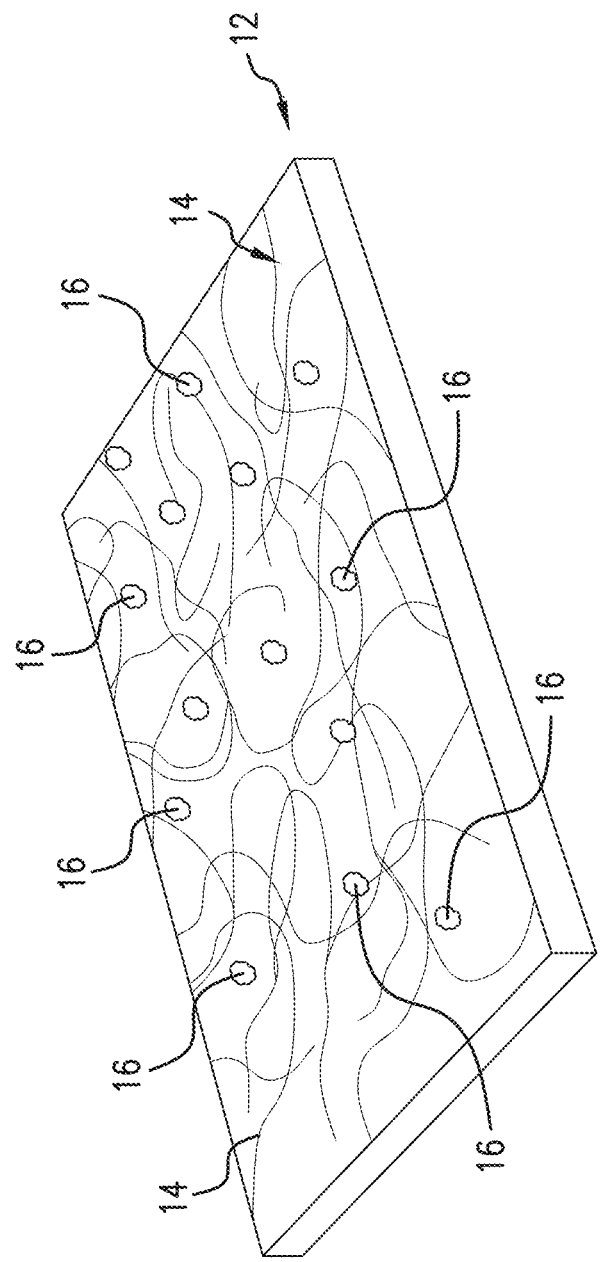
FIG. 1B is a perspective view of the sensing material of the solid state carbon dioxide sensor.

Referring to FIGS. 1A and 1B, solid state $CO_2$ sensor 10 of the present invention utilizes sensing material 12 formed with functionalized O-MWCNTs. Specifically, sensing material 12 is a composite that is composed of O-MWCNTs 14 and iron oxide ($Fe_2O_3$) nanoparticles 16. Sensing material 12 exhibits enhanced sensitivity as a gas sensing material due to a reaction that induces a modulation of surface charges. This enhanced sensitivity is a result of nano-heterojunction formations at the interface between the O-MWCNTs and iron oxide ($Fe_2O_3$) nanoparticles. Specifically, the iron oxide has mainly n-type semiconductor characteristics and MWCNTs have p-type semiconductor characteristics. These differences result in two depletion layers formed in such hybrid films. The first depletion region is located at the iron oxide surface and the second one is located at the interface between the iron oxide nanoparticles and the O-MWCNTs. The absorption of the $CO_2$ molecule induces a modulation of surface charges that directly influences the electronic transfer between the heterojunctions and induces a variation in the resistance of sensing material 12. Thus, sensing material 12 functions as a chemiresistor wherein the electrical resistance of sensing material 12 changes in response to increases in the concentration of $CO_2$ within the environment to which sensing material 12 is exposed. The presence of the iron oxide in the O-MWCNTs matrix also introduces nano-channels which play an important role in gas diffusion. The nano-channels allow the gas molecules to easily transport into the gas-sensing layers, leading to increasing $CO_2$ sensitivity.

FIG. 1A shows a cross-sectional view of a solid state $CO_2$ sensor in accordance with some embodiments of the present invention. Sensing material 12, which was described in the foregoing description, comprises O-MWCNTs 14 and iron oxide ($Fe_2O_3$) nanoparticles 16, which are illustrated in FIG. 1B.

Figure 1C:
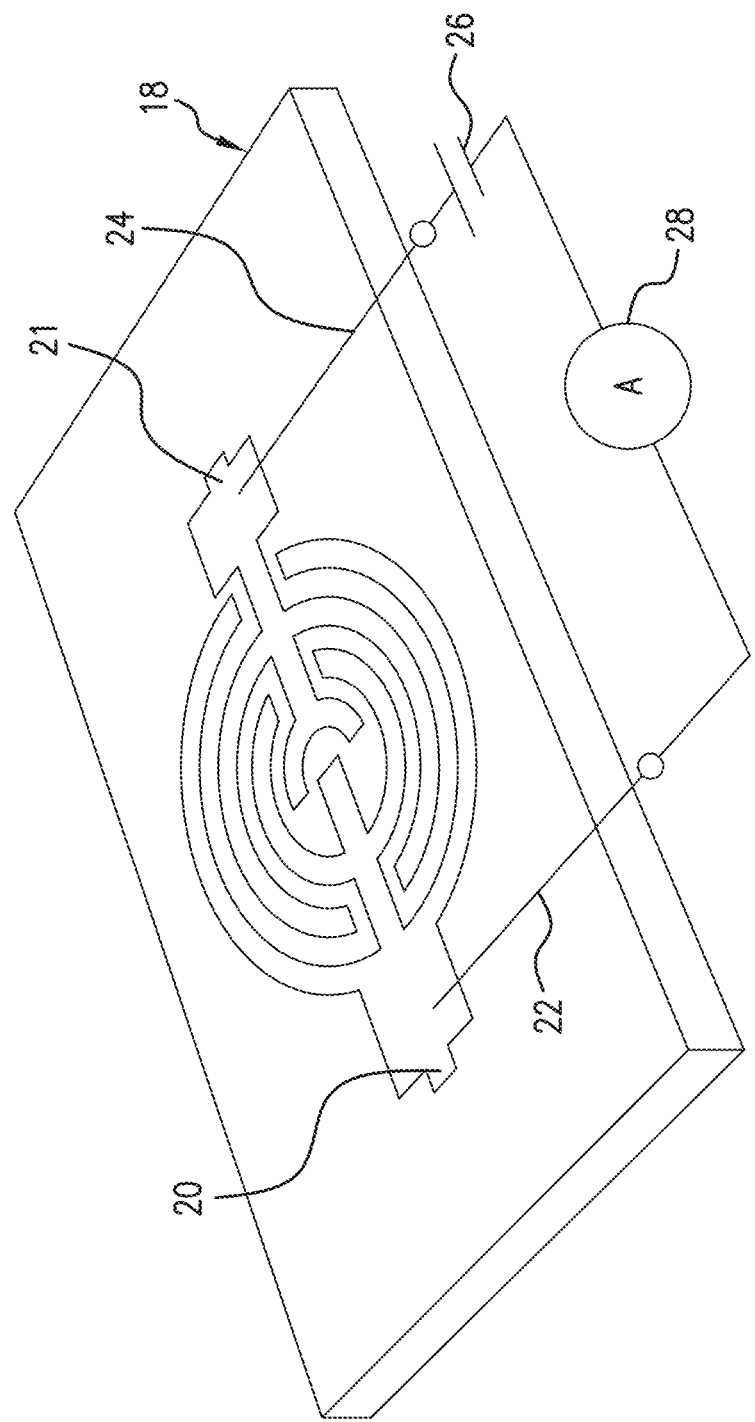
FIG. 1C is a perspective view of a substrate and interdigitated electrodes of the solid state carbon dioxide sensor.

Further with reference to FIG. 1A, $CO_2$ sensor 10 further comprises substrate 18 and electrodes 20 and 21, which are also shown in FIG. 1C. In an exemplary embodiment, substrate 18 is configured as a grade FR-4 printed circuit board (PCB). In some embodiments, substrate 18 is a rigid ceramic or silicon material. In an exemplary embodiment, electrodes 20 and 21 are configured as interdigitated electrodes and are micro-fabricated via screen printing on the surface of substrate 18. However, it is to be understood that any known suitable technique may be used to form electrodes 20 and 21 on substrate 18. For example, electrodes 20 and 21 may be formed on substrate 18 via gravure printing, flexographic printing, ink jet printing, aerosol jet printing, spraying and slot dye printing. Electrodes 20 and 21 may be formed from any suitable metals including, but not limited to, gold (Au), palladium (Pd), copper (Cu) and silver (Ag) and platinum (Pt). In an example embodiment, electrodes 20 and 21 are formed with gold (Au).

Further in FIG. 1C, solid state $CO_2$ sensor 10 includes electrically conductive output terminals or pins 22 and 24 that are electrically coupled to electrodes 20 and 21, respectively, and are adapted to be coupled to a circuit that can detect and measure changes in the electrical resistance of sensing material 12.

In an example embodiment, shown in FIG. 1C, output terminals 22 and 24 are electrically coupled to the series circuit formed by electrical power source 26 and electrical current measuring device 28. Electrical current measuring device 28 measures the electrical current passing through electrodes 20 and 21 as the concentration of $CO_2$ changes. In some embodiments, electrical current measuring device 28 is configured as a current meter. However, in other embodiments, electrical current measuring device 28 may be configured as any device or electronic circuit that can detect and measure the flow electrical current through electrodes 20 and 21. In some embodiments, power source 26 and current measuring device 28 are part of solid state $CO_2$ sensor 10. In other embodiments, power source 26 and current measuring device 28 are part of existing electronic circuitry or hardware with which solid state $CO_2$ sensor 10 is integrated. Since sensing material 12 functions as a chemiresistor, the electrical resistance of sensing material 12, which is measured via output terminals 22 and 24, changes in response to changes in the concentration of $CO_2$. Due to its unique structure and material composition, solid state $CO_2$ sensor 10 operates at room temperature and exhibits fast response times to concentrations of $CO_2$ ranging from 100 ppm to 0.5% $CO_2$ (OSHA maximum permissible exposure limit).

Figure 1D:
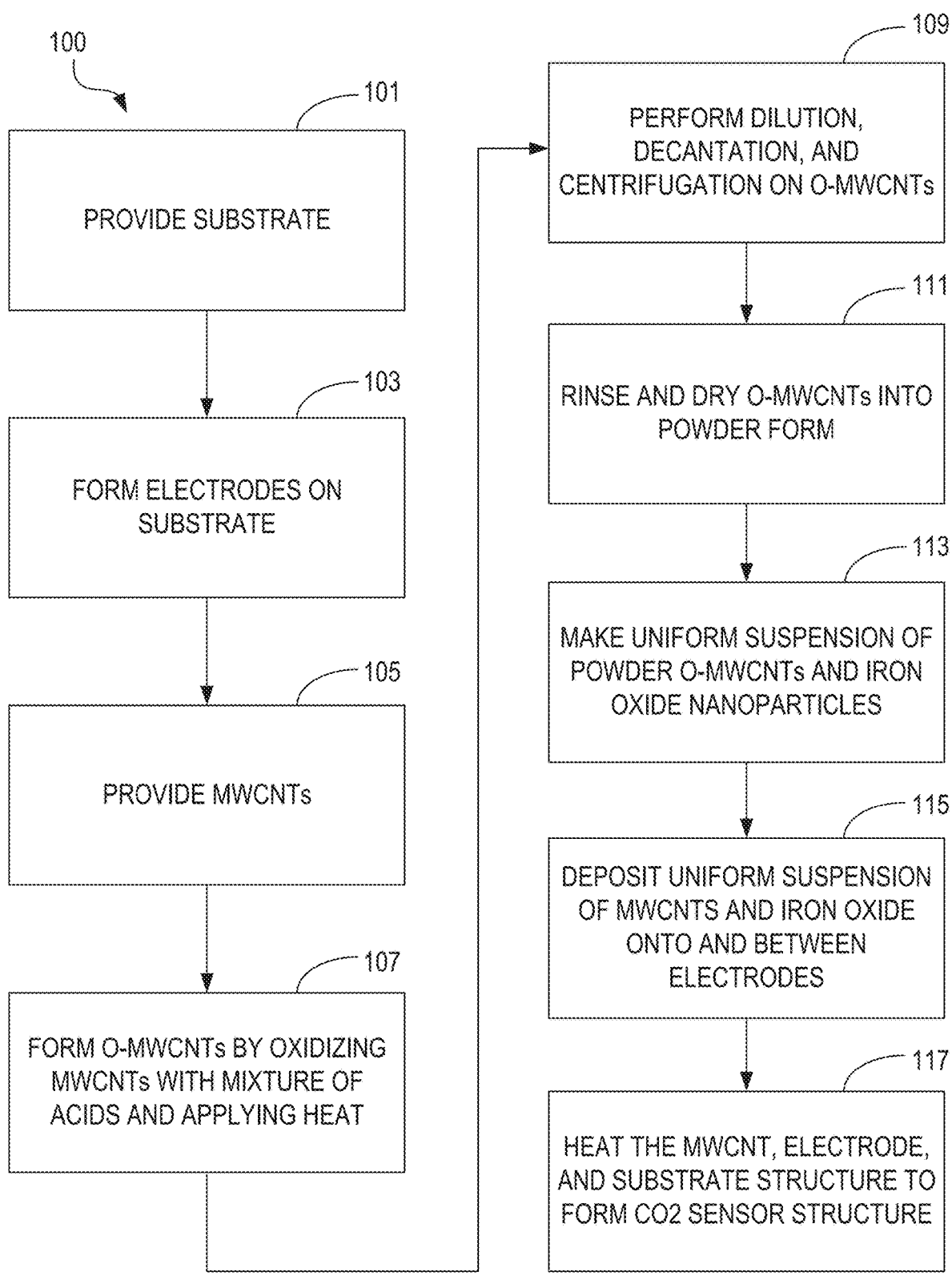
FIG. 1D is a flow diagram of a process for fabricating the solid state carbon dioxide sensor.

With reference to flow chart FIG. 1D, an example process 100 of fabricating the solid state $CO_2$ sensor of the present invention is providing substrate 18 at step 101. At step 103, electrodes 20 and 21 are formed on substrate 18 via any of the techniques described in the foregoing description. At step 107, O-MWCNTs are formed by providing an amount of MWCNTs, and then mixing the MWCNTs with a mixture of acids, then heating the mixture to oxidize the MWCNTs. In an example embodiment, the mixture of acids comprises concentrated sulfuric acid (98% $H_2SO_4$) and nitric acid (68% $HNO_3$) with the volume ratio of 3:1. In an example embodiment, oxidation is completed by exposure to a temperature at about 120° C. for a period of about 2 hours. At step 109, dilution, decantation and centrifugation are performed on the O-MWCNTs. If necessary, the dilution, decantation and centrifugation steps may be repeated. At step 111, the O-MWCNTs are then rinsed in water, and the purified O-MWCNTs are then dried at a predetermined temperature for a predetermined amount of time. In an example embodiment, the purified O-MWCNTs are dried at about 125° C. for about 3.0 hours using a programmable oven.

At step 113, the dry powder of the O-MWCNTs is then mixed with a predetermined weight percentage of iron oxide ($Fe_2O_3$) nanoparticles in water to make a uniform suspension. In some embodiments, the weight percentage of iron oxide ($Fe_2O_3$) in the uniform suspension is between about 3.25% and 3.75%. In an exemplary embodiment, the weight percentage of iron oxide ($Fe_2O_3$) in the uniform suspension is about 3.5%. It has been found that a weight percentage of about 3.5% iron oxide ($Fe_2O_3$) provides the optimal sensor performance for the detection of $CO_2$. It has further been found that the O-MWCNTs produce significantly more uniform suspension in water in comparison to non-oxidized MWCNTs. At this point, the uniform suspension is the liquid form of sensing material 12 described in the foregoing description.

At step 115, the uniform suspension of 3.5% iron oxide and O-MWCNTs in water is deposited via a micropipette onto interdigitated electrodes 20 and 21 and onto the gaps or areas between interdigitated electrodes 20 and 21. At step 117, the raw $CO_2$ sensor (i.e., substrate 18 with electrodes 20 and 21 covered with uniform suspension) is subjected to dehydration baking in a vacuum oven in order to heat and dry any water off the surface and leave a dry O-MWCNTs/iron oxide ($Fe_2O_3$) composite sensing material on the surface of interdigitated electrodes 20 and 21 and the gap areas between interdigitated electrodes 20 and 21. In an exemplary embodiment, the dehydration baking temperature is between about 200° C. and 400° C. and the dehydration baking time is between about 30-60 minutes. The dry O-MWCNTs/iron oxide ($Fe_2O_3$) composite layer functions as sensing material 12 of solid state $CO_2$ sensor 10 and is bonded to electrodes 20 and 21 and the gap areas between electrodes 20 and 21 via van der Waals force due to the large surface area and light weight of the carbon nanotubes.

Figure 1E:
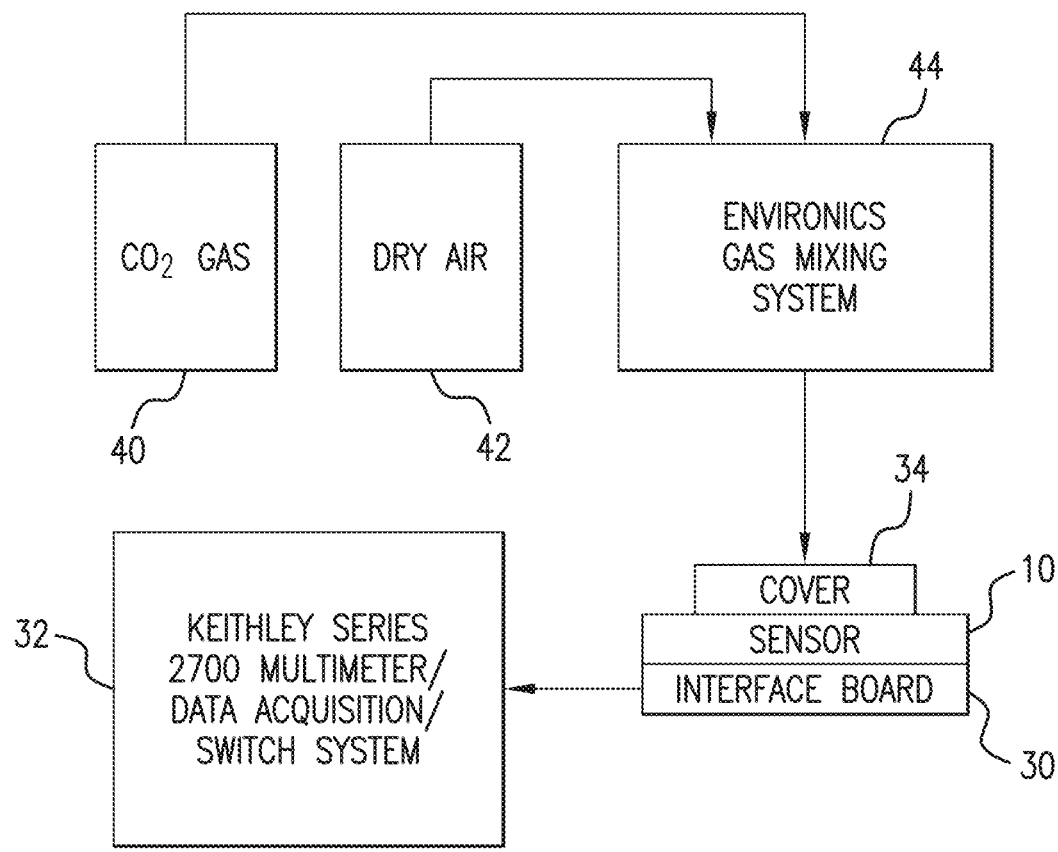
FIG. 1E is a block diagram of a system used to analyze the sensitivity of the solid state carbon dioxide sensor.
Figure 2:
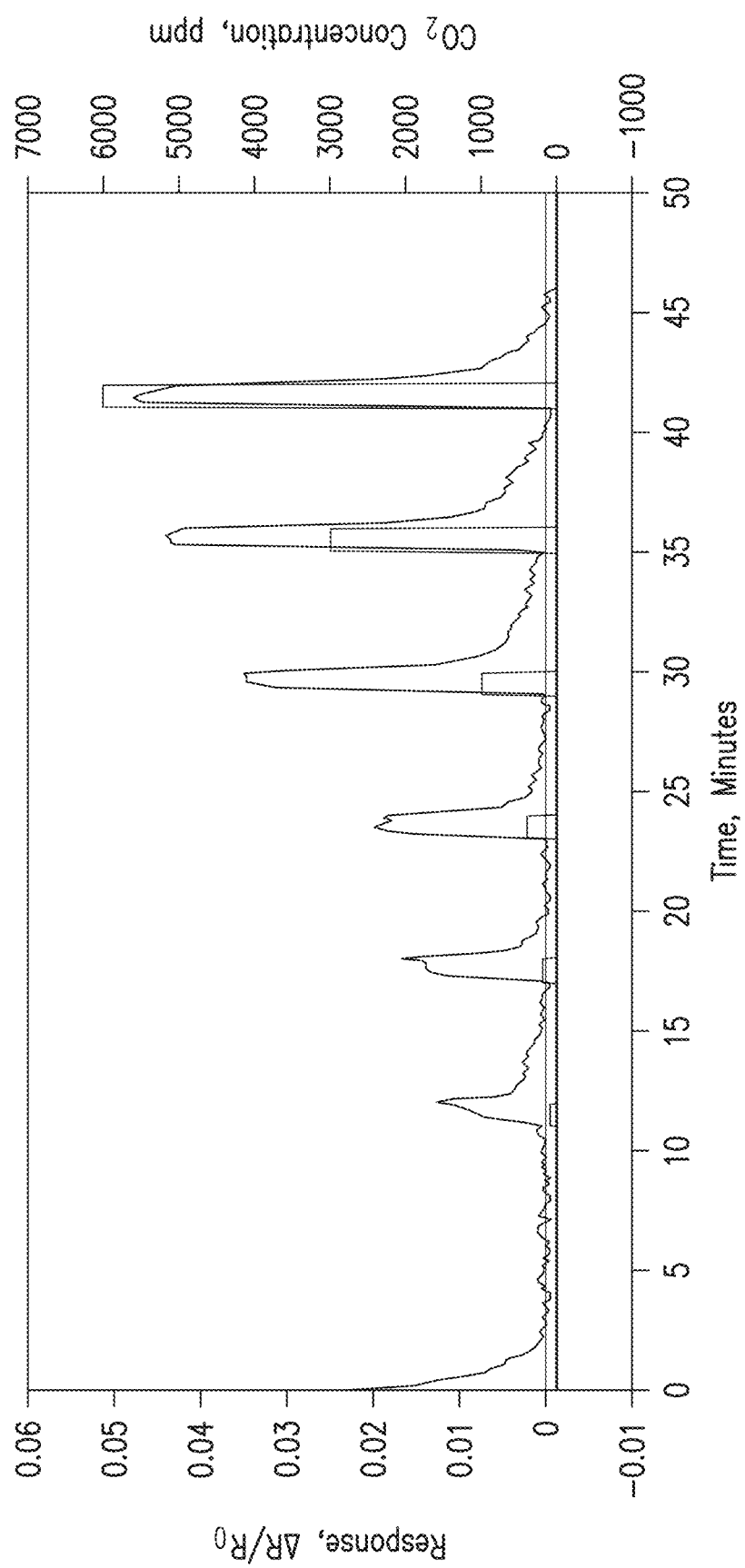
FIG. 2 is a plot of the responses of the solid state carbon dioxide sensor to increasing concentrations of $CO_2$ gas.

$CO_2$ gas exposure tests were conducted on $CO_2$ sensor 10 using the testing configuration shown in FIG. 1E. Output terminals 22 and 24 of $CO_2$ sensor 10 were electrically coupled to interface board 30. For this test, interface board 30 was a low-current scanner card. Interface board 30 is electrically coupled to a Keithley Series 2700 Multimeter/Data Acquisition/Switch System 32 which was set up to measure the electrical resistance of $CO_2$ sensor 10 during exposure to different amounts of $CO_2$ gas. The Keithley Series 2700 Multimeter/Data Acquisition/Switch System is manufactured by Keithley Instruments of Scottsdale, Ariz. In order to expose $CO_2$ sensor 10 to the $CO_2$ gas, Teflon cover 34 was positioned over $CO_2$ sensor 10. A nozzle (not shown) was attached to the interior of Teflon cover 34. The nozzle was adapted to introduce the stream of $CO_2$ gas directly onto the surface of $CO_2$ sensor 10. An Environics Gas Mixing System (Environics Inc., Tolland, Conn.) 44 was connected $CO_2$ gas source 40, dry air source 42 and to the nozzle (not shown) that is connected to Teflon cover 34. The $CO_2$ gas source 40 provided 10000 ppm $CO_2$. The dry air source 42 provided dry Zero Air. The Environics Gas Mixing System is a gas blending and dilution system and was used for introducing $CO_2$ gas at different concentrations to the nozzle within Teflon cover 34. Prior to exposing $CO_2$ sensor 10 to $CO_2$ gas, a stream of dry Zero Air was directed onto $CO_2$ sensor 10 for ten (10) minutes in order to establish a baseline resistance for the following $CO_2$ exposure and dry air flush cycles. Next, the Environics Gas Mixing System was activated so as to provide a gas stream of 400 cm$^3$/min to the nozzle inside Teflon cover 34 so as to expose $CO_2$ sensor 10 to $CO_2$ gas. $CO_2$ concentrations were run for a minute followed by a five (5) minute dry Zero Air flush. $CO_2$ concentrations were increased from 100 ppm to 6000 ppm. The tests were conducted at room temperature. FIG. 2 shows a plot of responses of $CO_2$ sensor 10 to the increasing concentrations of $CO_2$ gas. $CO_2$ sensor 10 exhibited high sensitivity. $CO_2$ sensor 10 also exhibited a stable base resistance of about 13000 Ohms thereby indicating $CO_2$ sensor 10 can be successfully integrated into existing electronics circuitry or hardware systems. Thus, $CO_2$ sensor 10 exhibited strong responses for high concentrations of $CO_2$ gas. $CO_2$ sensor 10 also exhibited low noise, quick response and quick recovery times as well as high repeatability or reproducibility of responses.

Figure 3:
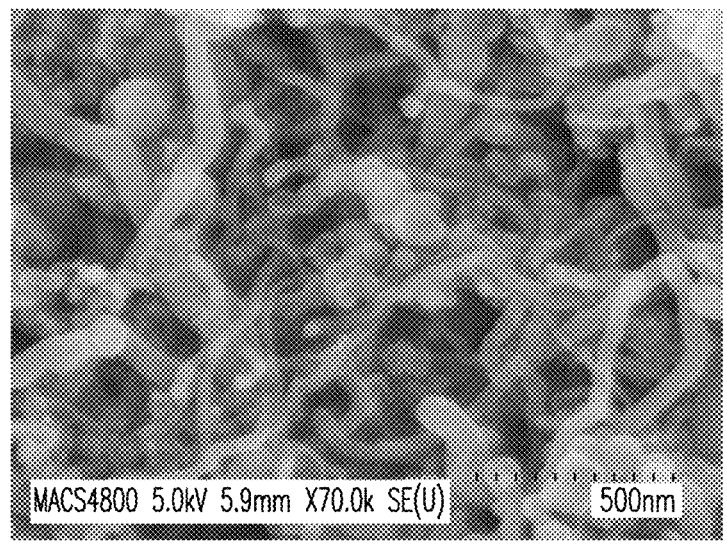
FIG. 3 is a FE-SEM image of the O-MWCNT/iron oxide composite sensing material of the solid state carbon dioxide sensor.

The morphology of the O-MWCNT, iron oxide ($Fe_2O_3$) nanoparticles and the nanocomposites of O-MWCNT/iron oxide ($Fe_2O_3$) that form sensing material 12 were investigated using a FE-SEM Hitachi S-4800 SEM. It has been found that the iron oxide ($Fe_2O_3$) nanoparticles formed chemical bonds with the oxidized MWCNT surface. Specifically, and as shown in FIG. 3, it can be seen that the MWCNTs form bundles due to the strong Van der Waals force. MWCNT diameters ranged from about 4 nm to about 10 nm. The morphology of the iron oxide image presents clusters of the iron oxides that cling together and form aggregates in spherical shapes with individual sizes ranging from about 5 nm to about 50 nm. The clusters of the iron oxide result from the magneto static coupling between particles. The SEM images of the O-MWCNT/iron oxide nanocomposites show networks of MWCNTs interwoven among the iron oxide nanoparticles. The iron oxide particles adhered on the surface of O-MWCNTs and formed small agglomerations as free particles. The iron oxide is distributed uniformly on the surface of the MWCNTs.

Figure 4:
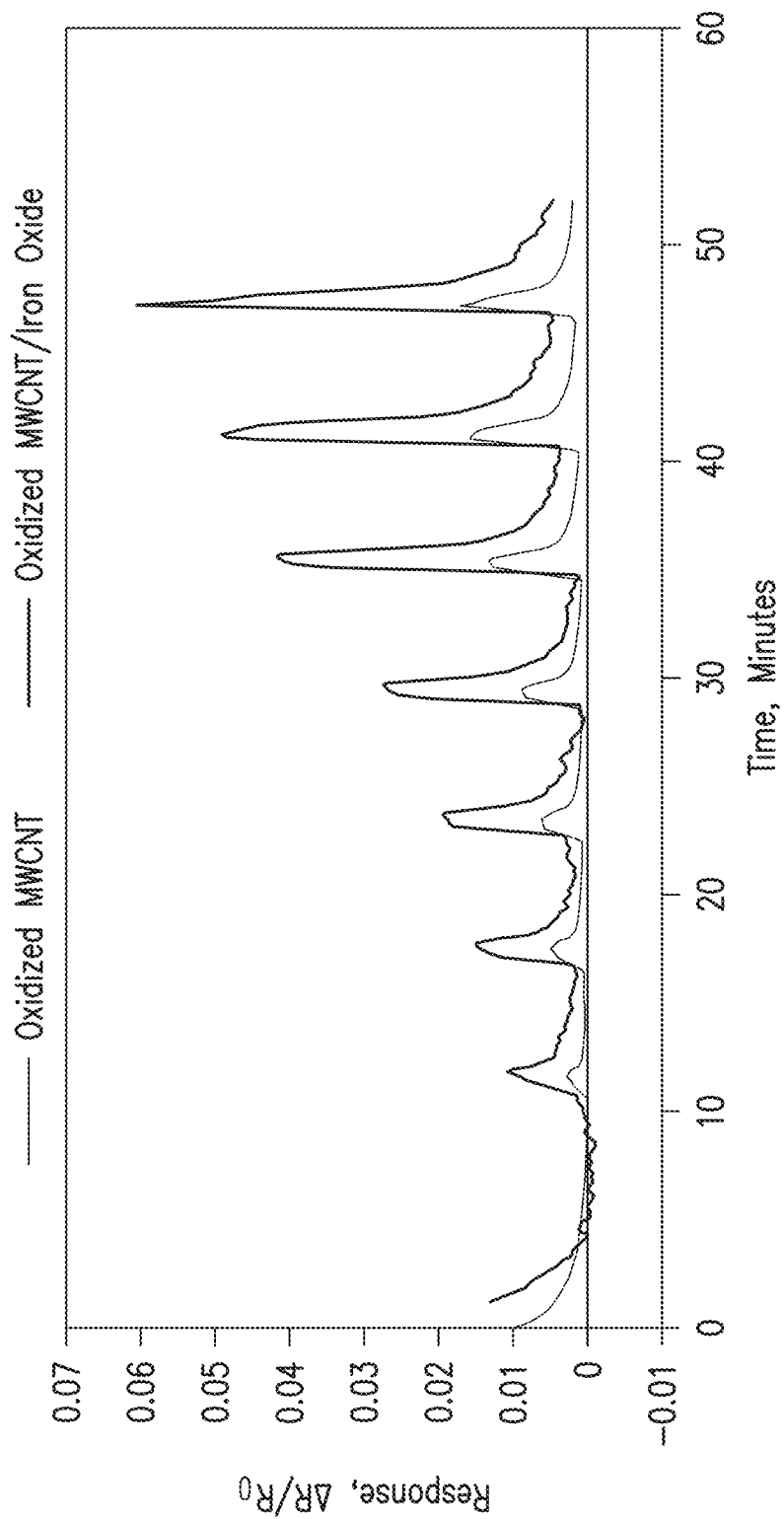
FIG. 4 shows the response curves for the solid state carbon dioxide sensor of the present invention and a conventional oxidized MWCNT-based sensor for various concentrations of $CO_2$.

The testing system shown in FIG. 1E was used to measure the electrical resistance of $CO_2$ sensor 10 and an O-MWCNT-based sensor without iron oxide ($Fe_2O_3$) nanoparticles. The O-MWCNT-based sensor without iron oxide ($Fe_2O_3$) nanoparticles had a resistance of about 1300 ohms. $CO_2$ sensor 10 had an average base resistance of about 13000 Ohms. The testing system shown in FIG. 1D was used to compare responses of $CO_2$ sensor 10 and an O-MWCNT-based sensor without iron oxide ($Fe_2O_3$) nanoparticles. Both sensors were exposed, at room temperature, to $CO_2$ concentrations of 100, 200, 400, 800, 1600, 3800 and 6000 ppm at the same time intervals used to test $CO_2$ sensor 10 with the testing system of FIG. 1E as described in the foregoing description. FIG. 4 shows the response curves for $CO_2$ sensor 10 and the oxidized MWCNT-based sensor without ($Fe_2O_3$) nanoparticles. The response is normalized resistance $\Delta R/R_0$ wherein $R_0$ is the base electrical resistance with no $CO_2$ exposure and $\Delta R = R - R_0$ wherein R is the electrical resistance at time "t" with $CO_2$ exposure. Sensor resistance increased when exposed to various concentrations of $CO_2$ gas and the change in sensor resistance was concentration dependent. $CO_2$ sensor 10 exhibited a response that was about five (5) times greater than the O-MWCNT-based sensor without ($Fe_2O_3$) nanoparticles. This is the result of the $CO_2$ molecules being absorbed at both the MWCNT surface and the iron oxide nanoparticles. $CO_2$ sensor 10 exhibited a greater response range in comparison to the O-MWCNT-based sensor without ($Fe_2O_3$) nanoparticles. FIG. 4 also shows that $CO_2$ sensor 10 exhibited enhanced responses at $CO_2$ concentrations of 3800 ppm and 6000 ppm while the O-MWCNT-based sensor without ($Fe_2O_3$) nanoparticles did not show distinct peaks for $CO_2$ concentrations of 3800 ppm and 6000 ppm.

Figure 5:
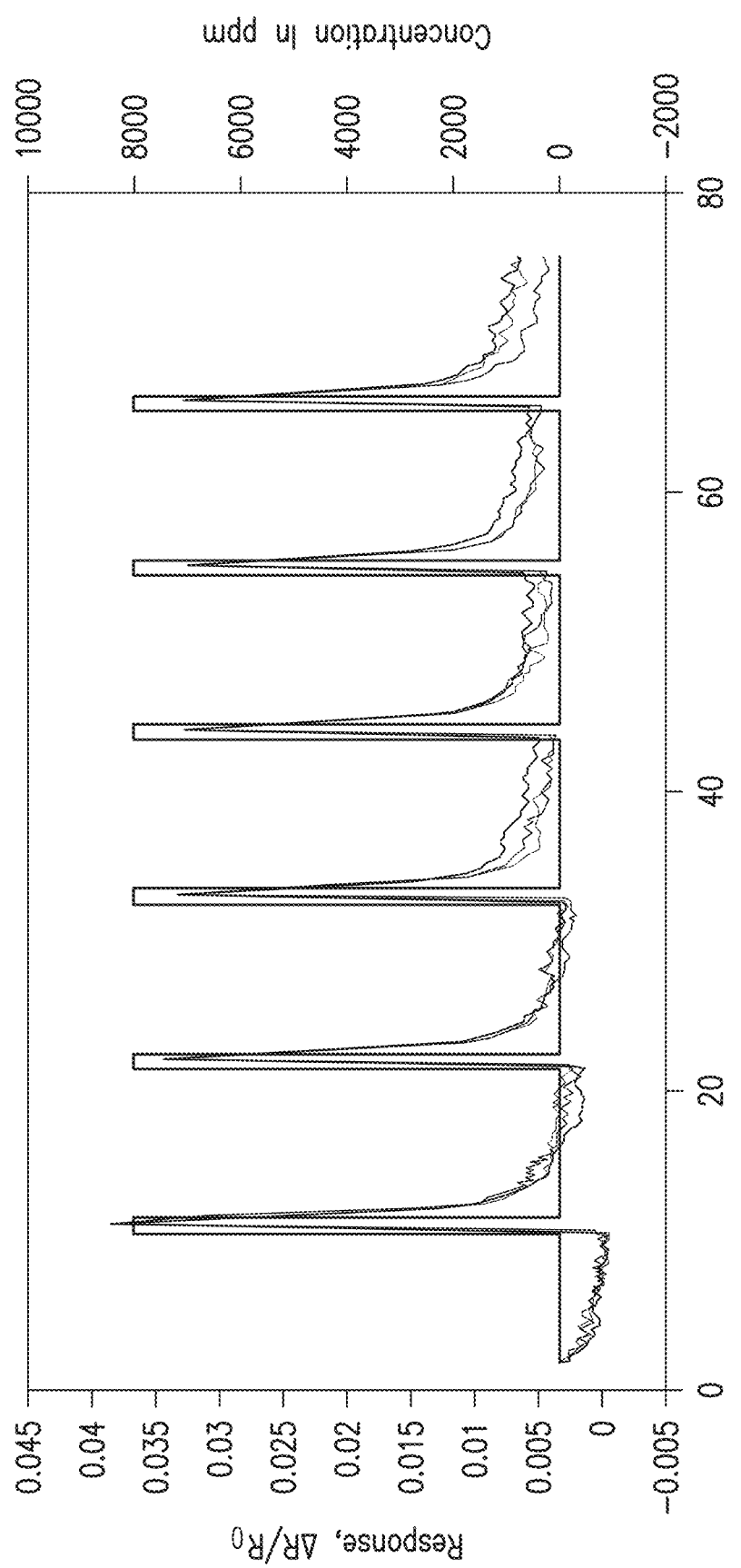
FIG. 5 is a plot of the responses of the solid state carbon dioxide sensor of the present invention for multiple exposures to a $CO_2$ concentration of 4000 ppm.

Referring to FIG. 5, there is shown a plot of the responses of $CO_2$ sensor 10 for multiple exposures of $CO_2$ at a concentration of 4000 ppm. The responses of $CO_2$ sensor 10 were all between about 0.0325 and about 0.0385.

The solid state $CO_2$ sensor of the present invention provides many benefits and advantages. For example, the $CO_2$ sensor has a rapid response time and can provide sensor outputs in seconds. The $CO_2$ sensor has high $CO_2$ sensitivity and can measure $CO_2$ having a concentration within the range of about 100 ppm and 10000 ppm. It has been found that the $CO_2$ sensor of the present invention has up to about five (5) times higher sensitivity to $CO_2$ than a MWCNT-based sensor without iron-oxide particles. The $CO_2$ sensor of the present also exhibits rapid recovery, decreased noise and reproducibility of responses. The $CO_2$ sensor of the present invention operates at room temperature, 25° Celsius, unlike conventional metal oxide sensors which must operate at ~300° Celsius. The $CO_2$ sensor of the present embodiments also operates in high humidity conditions (>80% RH) and in static diffusion mode conditions and dynamic flow mode conditions (e.g., 400 ccm). The $CO_2$ sensor of the present invention has a small footprint. Specifically, $CO_2$ sensor 10 can have a relatively small size of 0.5 cm×0.5 cm×3 mm with multiple sensors formed on substrate 18. Such small sensor size is in stark contrast to the smallest sized conventional NDIR sensor which is 2.5 cm.×1.25 cm.×1.25 cm. The solid state $CO_2$ sensor of the present invention is light in weight, weighting only a few grams. Another important benefit of the solid state $CO_2$ sensor of the present invention is that it consumes relatively less power. Specifically, less than fifty (50) microwatts are required for power since $CO_2$ sensor 10 functions on changes in resistivity. On the other hand, many conventional sensors function on optical properties or changes in capacitance. Auxiliary electrical output terminals 22 and 24 are built into solid state $CO_2$ sensor 10 and allow $CO_2$ sensor 10 to be easily integrated or coupled into existing electronic circuitry. Since the $CO_2$ sensor 10 is solid state, no consumables or extra materials are required to maintain operation. The solid state $CO_2$ sensor 10 does not require calibration as often as conventional $CO_2$ sensors and the calibration of the $CO_2$ sensor 10 can be automated. Another significant benefit is that per/unit manufacturing costs of the solid state $CO_2$ sensor is significantly less than per/unit manufacturing costs of many conventional $CO_2$ sensors. Another significant benefit is that due to the homogenous nature of the sensing material, the sensor-to-sensor variation is negligible thereby making the sensor suitable for large scale commercial production.

Figure 6:
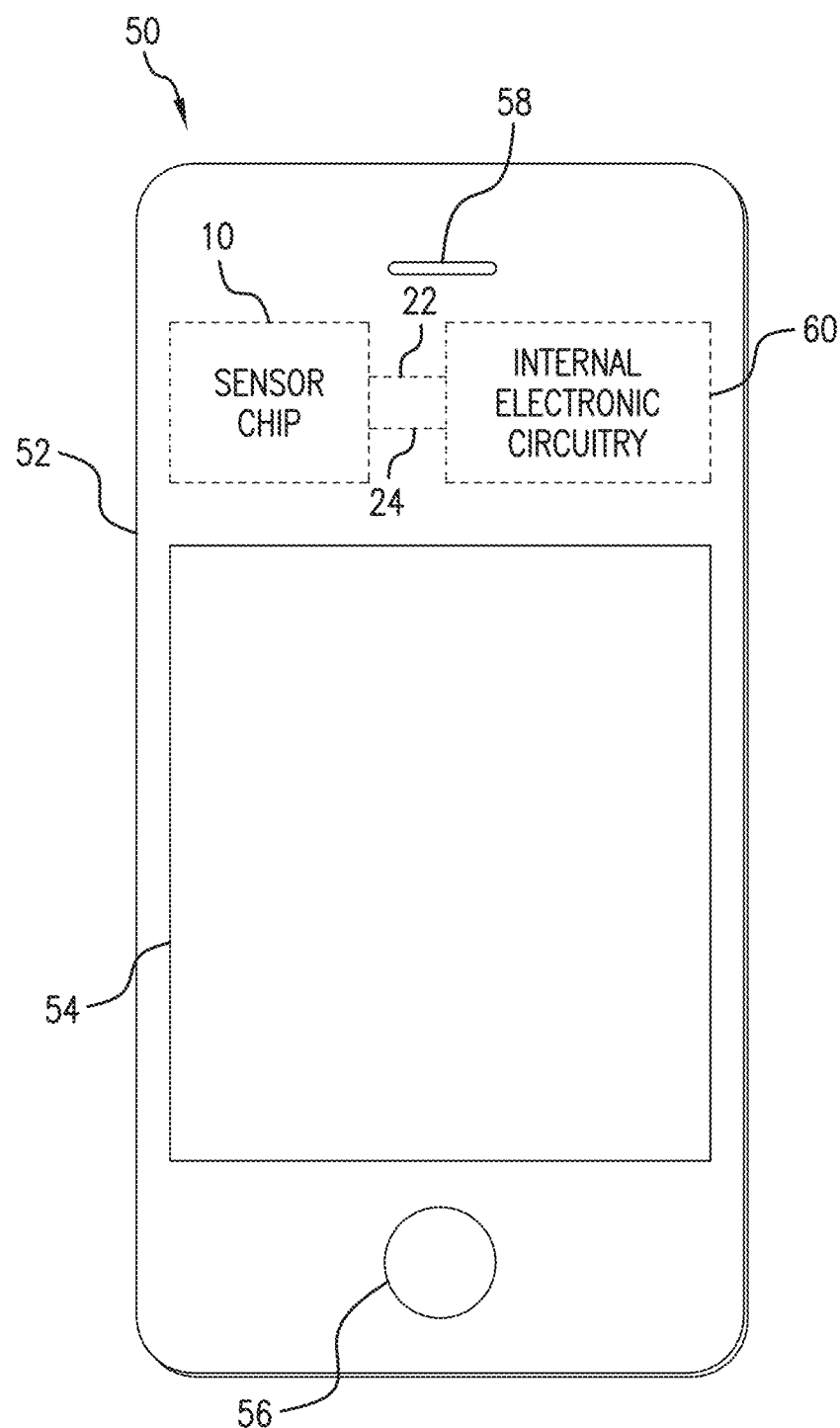
FIG. 6 is an exemplary schematic diagram of a smart phone incorporating the solid state carbon dioxide sensor of the present invention.

In some embodiments of the present invention, $CO_2$ sensor 10 is integrated into a smart phone to detect $CO_2$ gases in real time. One such an embodiment is shown in FIG. 6. Smart phone 50 comprises casing 52, display screen 54, home button 56 and speaker port 58, all of which are known in the smart phone industry. Internal electronic circuitry 60 in smart phone 50 is programmable and includes data acquisition circuitry that is coupled to electrically conductive output terminals 22 and 24 of $CO_2$ sensor 10 and is configured for detecting and measuring the electrical current flow through the electrodes 20 and 21. Smart phone 50 is programmed with an APP (i.e. mobile App) that determines if the detected current flow represents a concentration of $CO_2$ that exceeds a predetermined concentration of $CO_2$ and alerts a user if it is determined that the concentration of $CO_2$ exceeds the predetermined concentration of $CO_2$. In an exemplary embodiment, if the measured concentration of carbon dioxide exceeds the predetermined concentration, internal electronic circuitry 60 controls display screen 54 to display a message informing the user of the concentration of $CO_2$. In another exemplary embodiment, if the concentration of $CO_2$ exceeds a predetermined or preset level, then internal electronic circuitry 60 generates an audio alarm. In some embodiments, the audio alarm will continue until the user deactivates the audio alarm by touching the appropriate icon on display screen 54. Internal electronic circuitry 60 includes additional data processing circuitry and data storage circuitry that also execute and implement normal or typical smart phone functions. Integrating $CO_2$ sensor 10 into smart phone 50 provides many advantages, including a low cost signal processing platform, compactness, low power consumption, easy operation, rapid sensing and network sensing capability.

The $CO_2$ sensor of the present invention may be used to detect low concentrations of $CO_2$ at room temperature and with low power consumption. There are many space applications in which the $CO_2$ sensor of the present invention may be used. For example, the $CO_2$ sensor of the present invention may be placed or positioned in the crew cabin of the International Space Station (ISS) in order to continuously monitor real-time $CO_2$ concentrations for permissible exposure limit levels. If the real-time $CO_2$ concentrations exceed the permissible exposure limit levels, then the space life support system would be deployed to scrub the station atmosphere. In another space application, the $CO_2$ sensor of the present invention can be used to determine the catalyzing efficiency of the $CO_2$ splitting process on the planet Mars. This process is known as in-situ resource utilization and is necessary to produce breathing oxygen for astronauts. In some embodiments, the $CO_2$ sensor of the present invention is configured as a wearable sensor. In one such an embodiment, $CO_2$ sensor 10 is integrated with an RFID (radio frequency identification) platform so as to enable the wearable sensor to be used for astronaut atmospheric monitoring inside the astronaut's helmet. The $CO_2$ sensor of the present invention may be configured as a miniature "Lick and Stick" smart $CO_2$ sensor.

The foregoing description, for purpose of explanation, has been described with reference to specific embodiments. However, the illustrative discussions above are not intended to be exhaustive or to limit the invention to the precise forms disclosed. Many modifications and variations are possible in view of the above teachings. The embodiments were chosen and described in order to best explain the principles of the invention and its practical applications, to thereby enable others skilled in the art to best utilize the invention and various embodiments with various modifications as are suited to the particular use contemplated.

What is claimed is:

1. A method of fabricating a sensor for sensing carbon dioxide ($CO_2$), comprising: providing a substrate; disposing a pair of electrodes on the substrate; providing a predetermined amount of multi-walled carbon nanotubes (MWCNTs); oxidizing the MWCNTs with a mixture of acids at a first predetermined temperature and for a first predetermined amount of time; diluting, decanting and centrifuging the oxidized multi-walled carbon nanotubes (O-MWCNTs); rinsing the O-MWCNTs in water to produce purified O-MWCNTs; drying the purified O-MWCNTs at a second predetermined temperature for a second predetermined amount of time to produce purified O-MWCNTs in dry powder form; forming a solution consisting of water, the purified O-MWCNTs in dry powder form and iron oxide ($Fe_2O_3$) nanoparticles so as to produce a uniform suspension; depositing the uniform suspension onto the electrodes; and thereafter, baking the substrate so as to transform the uniform suspension into a dry ($CO_2$) sensing material.

2. The method according to claim 1 wherein the step of disposing a pair of electrodes on the substrate comprises forming a pair of interdigitated electrodes on the substrate.

3. The method according to claim 1 wherein the mixture of acids comprises sulfuric acid and nitric acid.

4. The method according to claim 1 wherein the weight percentage of iron oxide (Fe2O3) nanoparticles in the solution is between 3.25% and 3.75%.

5. A sensor made according to the method of claim 1.

* * * * *